United States Patent [19]

Monjour et al.

[11] Patent Number: 4,992,273

[45] Date of Patent: Feb. 12, 1991

[54] ANTIGENS OF LEISHMANIA PARASITES

[75] Inventors: Louis Monjour, Paris; Alberto Roseto, Chatou; Armand Berneman, Paris; Marie-Claude Guillemin-Debons, Chatou; Martine Domurado, Grandfresnoy; George Peries, Paris, all of France

[73] Assignees: Institut Pasteur, Paris; Universite de Technologie de Compiegne, Compiegne; Universite Pierre Et Marie Curie, Paris, all of France

[21] Appl. No.: 878,876

[22] PCT Filed: Sep. 26, 1985

[86] PCT No.: PCT/FR85/00264

§ 371 Date: Jul. 31, 1986

§ 102(e) Date: Jul. 31, 1986

[87] PCT Pub. No.: WO86/02098

PCT Pub. Date: Apr. 10, 1986

[30] Foreign Application Priority Data

Oct. 1, 1984 [FR] France .................................. 84 15079
Feb. 11, 1985 [FR] France .................................. 85 01892

[51] Int. Cl.$^5$ .................................................. A61K 39/8
[52] U.S. Cl. ........................................ 424/89; 424/85.8; 424/88; 435/240.27; 530/387; 530/395
[58] Field of Search .................... 424/85, 88; 530/387, 530/395; 435/240.27

[56] References Cited

PUBLICATIONS

Monjour, et al., C. R. Acad. Sc. Paris, +.300, Série III, No. 9, 1985, pp. 395–398.

Jaffe et al., *The Journal of Immunology*, vol. 133, No. 1, pp. 440–447 (1984).

Jaffe et al., *The Journal of Immunology*, vol. 131, No. 4, pp. 1987–1993 (1983).

Handman et al., *Chemical Abstracts*, vol. 98, p. 273, 157503n (1983).

Sheppard et al., *The Journal of Immunology*, vol. 131, No. 3, pp. 1496–1503 (1983).

Pratt et al., *Nature*, vol. 291, No. 5816, pp. 581–583 (1981).

Guesdon et al., *Journal of Immunological Methods*, vol. 39, pp. 1–13, (1980).

Handman et al., *Infection and Immunity*, vol. 37, No. 1, pp. 28–33, (1982).

Handman et al., *Parasite Immunology*, vol. 6, pp. 223–233, (1984).

*Primary Examiner*—Robert A. Wax
*Assistant Examiner*—Jeffrey Stucker
*Attorney, Agent, or Firm*—Fleit, Jacobson, Cohn, Price, Holman & Stern

[57] ABSTRACT

The invention concerns hybridomes producing anti-Leishmania monoclonal antibodies which are characterized by their capacity to inhibit the infection of sarcomatous cells by the promastigote forms of one or more species of Leishmania, when the sarcomatous cells are placed in contact with the said promastigote forms pre-incubated with these monoclonal antibodies under conditions which, in the absence of the said monoclonal antibodies, would lead to an elevated parasitemia in the said cells.

These monoclonal antibodies and the proteins of the parasites that they recognize may be used in the operations of leishmanioses detections.

10 Claims, No Drawings

ANTIGENS OF LEISHMANIA PARASITES

The invention is relative to new anti-Leishmania monoclonal antibodies and to hybridomes secreting such monoclonal antibodies. It concerns more particularly monoclonal antibodies susceptible to induce a protective activity with regard to a host sensitive to infection by the leishmanias and equally to recognize the polypeptides coming from these parasites and which are themselves recognized by serums obtained from hosts infected by various species of leishmanias. It concerns lastly antigens susceptible of being recognized by these antibodies and the utilization of these antigens for the constitution of vaccine compositions destined for Man or animals, notably dogs.

The leishmanioses encompass a complex group of infections which have in common to be caused by intracellular parasites of the genus Leishmania. One may refer to the preamble of the international patent application PCT/U.S. No. 82/01678, filed the 17th of Nov. 1982 and published under the No. WO83/01785, to have a general review of the different forms which these infections may assume and the different species of Leishmanias which cause them. The development of these infections as much in third world countries as in industrialized countries is all the more worrying since at the present time the means are few for combating the different infections caused by these parasites and to check their extension into new territories. The therapeutic arsenal is limited and there does not exist at present any vaccination able to achieve an effective prevention without secondary complications.

The antigenic diversity of the leishmanias has been demonstrated notably by the utilization of monoclonal antibodies. One will note on this subject, other than the aforementioned international patent application the works realized by D. McMAHON PRATT and John R. DAVID, (1981), Nature, Vol. 291, 581-583; by E. HANDMAN and R. E. HOCKING (1982), Infections and Immunity, 28-33; by E. HANDMAN, H. M. JARVIS and G. F. LITCHELL (1984) Parasite Immunology, 6, 223-233. The overall impression which comes out of the existing literature is precisely the great variety of the monoclonal antibodies which have been made, these monoclonal antibodies ought to permit precise identifications hereafter of the different existing species and sub-species of Leishmanias. Publications describing the protection effects to a living host against certain species of leishmanias are much rarer. One could cite nevertheless the results of in vivo protection by monoclonal antibodies against the promastigotes of *Leishmania mexicana* which have been obtained by ANDERSON and coll. (1983) The Journal of Immunology, 131, 1616-1618, on the occasion of the implementation of a test called the "Winn assay system". The principle of this test is described in an article by H. J. WINN (1960) published in the "J. of Immunology", Vol. 84, p. 530.

The invention proceeds from a different process. Indeed, it had as its aim the production of monoclonal antibodies (or of compositions based on several types of monoclonal antibodies) which should be capable, on the one hand, of recognizing the antigenic determinants common to the various leishmania species, on the other hand, to involve a protective effect in vivo against these diverse species. Another objective was the isolation of one or several antigens susceptible of inducing in the host to which they may be administered the aquisition of a global immunity, consequently equally a global protection against the different cutaneous, mucocutaneous and visceral leishmanioses of the Old and New world.

More particularly still, the invention has for its aim to provide a process permitting to conduct the selection of the antibody-secreting hybridomes towards those which will be capable of producing monoclonal antibodies responding to the above-indicated characteristics.

The anti-Leishmania monoclonal antibodies according to the invention are characterized by their capacity to inhibit the infection of sarcomatous cells by promastigote forms of one or more species of Leishmania, when these sarcomatous cells are placed in contact with the said promastigote forms pre-incubated with these monoclonal antibodies, under conditions which, in the absence of the said monoclonal antibodies, would lead to a high parasitemia in the said cells.

A process for the obtaining and isolation of hybridomes secreting anti-leishmania monoclonal antibodies possessing the properties indicated above is characterized in that one places in contact the infectious promastigote forms with, on the one hand, monoclonal antibodies recognizing the antigens of one or several leishmania species and secreted among the hybridomes previously formed in a fashion in itself known between myeloma cells and spleen cells of an animal, notably the mouse, previously immunized against one or several leishmania strains and, on the other hand, with sarcomatous cells under conditions which, in the absence of the said antibodies, would lead to a parasitic infection of the said sarcomatous cells, and in that one selects those of these monoclonal antibodies which, in the preceding operation, completely protect in vivo the sarcomatous cells vis-à-vis infection by the said leishmanias, after their injection into the peritoneum of a mouse sensitive to said sarcomatous cells, more particularly a Balb-C mouse. Preferably—but not necessarily—the promastigote forms used are pre-treated with the monoclonal antibodies in the Balb-C mouse. This pre-treatment consists preferably of a contact maintained at 37 degrees C., for 30 minutes. The possible infection of the said sarcomatous cells may be appreciated by the removal of the ascites, when this is formed in the peritoneal cavity of the mouse, culturing of the sarcomatous cells of the ascites in an appropriate medium, for example NNN medium, and possible detection of the promastigotes formed in the medium. It goes without saying that the selection of the secreting hybridomes is in direct rapport with that of the protecting monoclonal antibodies.

It results from the preceding that the invention brings into play the capacity of the monoclonal antibodies finally selected, for exercising an effective protective activity vis-à-vis cells particularly sensitive to parasitic infection. The sarcomatous cells known under the designation "TG180" described by SARTORELLI, A. C. and BOTH, B. A. (1961) Federation Proceedings, 20, 156-159, proved to be so sensitive that one has proposed using them for the rapid production and in large quantity of leishmanias, more particularly under their amastigote form (intracellular form of leishmanias). The conditions of this production and the isolation of the leishmanias described have been described by L. MONJOUR et coll. in the article entitled "Rapid, Large-scale Production and Isolation for Leishmania Amastigotes", Annals of Tropical Medicine Parasitology (1984), 78, 423–425. In addition, these TG180 cells produce an ascites when they are injected into a Balb-C mouse; consequently the least of infected sarcomatous cells will amplify in the mouse the response to the infection in multiplying the infected cells and in propagating the infection to at least all of the ascites.

The invention results therefore from a research orientation based on the initial hypothesis which has been made (and which has proved fertile) that it should be possible to produce and to isolate anti-Leishmania monoclonal antibodies capable of protecting cells normally so sensitive to parasitic infection. This hypothesis went thus equally to furnish the essence of the particularly rigorous test which constitutes the foundation of the process for the production and selection of the producing monoclonal antibodies conforming to the invention.

The invention concerns therefore more particularly monoclonal antibodies characterized by the capacity they have to inhibit parasitic infection of cells of the TG180 line, when $2 \times 10^3$ cells of this line are injected into the peritoneum of Balb-C mice mixed with 60 microliters of ascites containing the aforesaid monoclonal antibodies and $10^5$ promastigotes which have been previously incubated in the presence of the said monoclonal antibodies at 37 degrees C. and for 30 minutes. In the absence of the protecting monoclonal antibodies, such a treatment will lead to an acute parasitemia of the cells. These quantitative indications determine equally the preferred conditions of the selection test which is used in the process according to the invention.

The monoclonal antibodies used in the operations of infection of sarcomatous cells in view of the selection of protective monoclonal antibodies resulting preferably already from a pre-selection. As has been indicated above, the monoclonal antibodies used are those which recognize the antigens of one or several species of leishmania.

This pre-selection may be realized in any of the ways in themselves known, for example under the conditions which follow (and of which, in addition, an example of its detailed operation will be indicated further on in the example).

Starting from one or more chosen parasite species, one immunizes an animal, notably the mouse, with the parasites under the promastigote form and one realizes a cellular fusion of spleen cells of the previously sacrificed animal with the appropriate myeloma cells, essentially according to the method described by KOHLER G. and MILSTEIN C. (1975), Nature, 256, 496–497. The hybrid cells producing antibodies may then be cloned by any method in itself known, preferably by the method of limit dilutions. The hybridomes finally selected were then used in the production of ascites, preferably by the technique described by ROSETO A. and Coll. (1983), Journal of Virology, 64, 237–244. The determination of IgG classes is then realized preferably by the method of immunodiffusion, described by ROSETO A. and Coll. (1982), Comptes Rendus de l'Académie des Sciences Paris, 294: 347–352. By preference, one collects the hybridomes secreting monoclonal antibodies belonging to the IgG class of immunoglobulins and one sorts through the supernatants of the clone cultures obtained or the corresponding ascitic liquids, according to the method described by MONJOUR L. and Coll. in "Annales de la Société Belge de Médecine Tropicale" (1978), 58: 293–300, to retain in a first step (on the majority) only the monoclonal antibodies which bind several leishmanias at a time, advantageously onto at least one of the parasites belonging to each of the species L. infantum, L. tropica, L. brasiliensis and L. mexicana (detection of the binding by global indirect immunofluorescence) and, at the end of the second sorting, those of the monoclonal antibodies which bind onto the living or killed parasites.

It is evident that one may equally use any other protocol for the production and selection of monoclonal antibodies apt to recognize the living or killed parasites. It should in addition be pointed out that the selection of the monoclonal antibodies among those which present the characteristics of the IgG immunoglobulins is in no way obligatory.

The use in the process according to the invention of one or several anti-Leishmania monoclonal antibodies thus previously selected may lead not only to the monoclonal antibodies protecting against those of the parasite species initially used (on the occasion of the immunization of the animals, from which the spleen cells have then been used for the production of these monoclonal antibodies), but again against different leishmania species. It is in this regard remarkable that the operation of the process according to the invention starting from several parasite species permits the isolation of monoclonal antibodies recognizing one or more antigens which prove to be common to a great number of leishmania species.

In particular, the operation of the process according to the invention under conditions which will be described further on permits the isolation of monoclonal antibodies recognizing the antigens, proteins or glycoproteins having (for certain of these monoclonal antibodies) molecular weights of the order of 40,000, 70,000 and 113,000 and, for other monoclonal antibodies, antigens or proteins having molecular weights of the order of 140,000 (precision of the order of 10%), all these antigens or proteins being obtainable from lysates of leishmanias, notably under the conditions which will be recalled further on.

Similar tests repeated on other lysates have in addition made it apparent that one may also isolate from the lysates of these diverse leishmania species, the antigens which are protective (or susceptible of inducing the in vivo production of productive antibodies having much smaller molecular weights, notably less than or equal to 30,000 kD, or even less than 20,000 kD.

The tests the results of which are reported further on make apparent the glucidic nature of certain of the protective antigens concerning the invention.

Thus it has been observed that the protective antigen of 70 kD, which may be obtained from the aforesaid lysates, contains glucose and mannose groups, and that the protective antigens present molecular weights respectively of 20 and 30–32 kD including fucose and alpha-D-L-acetyl-galactosamine groups.

The process according to the invention may therefore, at the level of the infection of the sarcomatous cells, be used with monoclonal antibodies of which has been recognized the capacity in the course of the prior selections, of recognizing the antigens of different species. As an alternative, one may equally use, at the level of the infection mixtures of monoclonal antibodies obtained from pre-selected hybridomes and having brought into play Leishmanias belonging to different species at the level of the initial immunization. For example, one uses at the level of the infection a mixture of monoclonal antibodies obtained from hybridomes which have themselves been obtained by hybridization between myeloma cells and spleen cells coming from mice which have been immunized respectively by L. mexicana, L. infantum, L. tropica, L. brasiliensis and L. donovani. When one has determined the capacity of a given mixture of monoclonal antibodies to protect the sarcomatous cells against infection in vivo by a plurality of given parasites, one may again repeat the test of protection with each of the given monoclonal antibodies contained in the mixture, in view of searching for that which is more particularly capable of protecting the sarcomatous cells against the set of the said parasites and consequently to isolate the corresponding hybridome.

The methods proposed above are only indicative of all those which may be used to demonstrate or isolate the polypeptides bearing the antigenic sites intervening in the antigen-antibody reaction. The techniques of genetic recombination could equally be used to the same ends.

The polypeptides recognized by the antibodies according to the invention may, especially when they are common to several species of leishmanias, be utilized for the production of pharmaceutic compositions intended for vaccination against the leishmanioses. These polypeptides are then associated with them with physiologically acceptable vehicles appropriate to the vaccination methods. Advantageously these pharmaceutic compositions are constituted in a fashion appropriate to administration by injection.

The preferred supplementary characteristics of the invention will appear yet in the course of the description which follows of the preferred conditions which have been used for the production, the selection and the isolation of the hybridomes conforming to the invention.

1. PARASITES

One has used the promastigote forms of the following species: L. infantum LEM 497, L. tropica LEM 129, L. brasiliensis quyanensis LEM 311 and L. mexicana amazonensis LV 79 for the characterization of the antigens recognized by the antibodies. In addition to these strains, the following strains have been used for the protection experiments: L. brasiliensis quyanensis: Cay H 60 and Cay H 53; L. donovani: ANTWERPEN, ITMAP 430 (Portugal), ITMAP 263 (Morocco), ITMAP 240-366 (Tunisia), ITMAP 1356 (Italy), LV 9 (Ethiopia), LEM 139 (India), L. mexicana mexicana LEM 280, L. tropica LV 39.

2. PRODUCTION OF INFECTIOUS PROMASTIGOTE FORMS $2 \times 10^3$ mouse sarcomatous cells (A. C. SARTORELLI and B. A. BOTH, Ped. Proc., 20, 1961, p. 156-159), named TG 180 (P. COUZINEAU and H. BAUFINE-DUCROC, Ann. Par. Hum. Comp. 44, 1969, 217-224) are mixed with $2 \times 10^6$ promastigote forms. After intraperitoneal injection into the Balb/c mouse, an ascites liquid is collected 7 to 10 days later. Centrifugation of this liquid gives a pellet of sarcomatous cells infected by the amastigote forms. After 4 days of culture in NNN medium at 22 degrees C., one obtains a proliferation of the promastigotes constantly infectious for the Balb/c mouse (L. MONJOUR, I. VOULDOUKIS, O. BRANDICOURT, D. MAZIER, D. ALFRED, I. PLOTON and M. GENTILINI, Ann. Trop. Med. Par. 1984, 78, 423-425).

3. PRODUCTION OF THE MONOCLONAL ANTIBODIES (a) Immunization of the mice

Balb/c mice are subjected to 3 sub-cutaneous injections, each spaced 15 days apart, with $10^6$ promastigotes of L. infantum mixed with 10 micrograms of a saponin-based immuno-adjuvant commercialized under the designation QUIL A. One month later, the mice are subjected to one last intraperitoneal injection of $2 \times 10^7$ promastigotes. Four days later, the mice were sacrificed and their spleen cells removed.

(b) Hybridomes

The fusion of the aforesaid spleen cells and myeloma SP2/0 cells, the culture of the hybrids, the detection of the monoclonal antibodies, their characterization by radial immunodiffusion and the production of ascites have been effected according to protocols previously described (A. ROSETO, T. F. VAUTHEROT, P. BOBULESCO and M. C. GUILLEMIN, C. R. Acad. Sciences Paris-294, 1982, p. 347-352).

(c) Demonstration of the antibodies

The secretion products of the hybridomes have been tested on promastigotes of the Old and of the New world, dead or alive. and this, by indirect immunofluorescence (L. MONJOUR, C. MILLE, P. DRUILHE. and M. GENTILINI, Ann. Soc. Belge Med. Trop., 58, 1978, p. 293-300). Ten ascites have produced a positive reaction against at least certain of the species of parasites identified in the table further on. Five ascites have proved to produce a positive reaction against each of the said parasite species.

4. INHIBITION TESTS

These tests have been conducted on several species of leishmanias of the Old and of the New world. Five monoclonal antibodies of the isotype IgG1, produced in ascites and reacting positively in immunofluorescence on the promastigotes, have been selected, then mixed for the inhibition tests. 60 microliters of the mixture have been placed in contact with $10^5$ promastigotes of one species, at 37 degrees C., for 30 minutes. $2 \times 10^3$ of TG 180 cells were then added; after washing, the mixture was injected intraperitoneally into the Balb/c mouse. 10 days later, the ascites formed was removed by aspiration with a syringe. The search for intra and extracellular amastigotes is done on a May-Grènwald-Giemsa stained preparation. The presence of promastigotes is revealed after 20 days incubation of the ascitic cells in NNN medium. The experimental controls are the following: anti-HBs and anti-Plasmodium falciparum monoclonal antibodies, supernatants of ascites provoked by the injection of pristane and myeloma SP2/0; another control consists of bringing into contact the ascites induced by the sarcomatous TG 180 with each species of the panoply of leishmanias, at 37 degrees C., for 30 minutes. Lastly, the pathogenic character of the species is proved by the infection, under the same conditions, of the sarcomatous cells with each species of Leishmania.

5. ANTIGENIC CHARACTERIZATION

The lysates of the different parasites, realized in the presence of protease inhibitors (PMSF and TLCK at $10^{-3}$M) have been analyzed, by immunoblotting onto nitrocellulose sheet (H. TOWBIN, T. STAEHELIN and I. GORDON, PNAS, U.S.A., 76, 1979, p. 4350-4354) of the electrophoretic profile by the technique of Laemmli (V. K. LAEMMLI, Nature, 227, 1970, p. 680-683) on 10% acrylamide gel. The antigen-antibody complexes have been revealed by anti-antibodies labeled with peroxydase according to Avrameas (S. AVRAMEAS and B. GUILBERT, Eur. J. Imm., 1, 1971, 394-396).

The molecular weights of the antigens have been appreciated by their migration distances in the gel, compared to the following proteins of known molecular weights: ferritin (220 kD), ovotransferin (77 kD), bovine albumin (67 kD), catalase (60 kD), ovalbumin (45 kD), lactate dehydrogenase (36 kD), chymotrypsinogen A (25.7 kD), ferritin (monomeric form) (18.5 kD), myoglobulin (17.2 kD), cytochrome c (12.3 kD).

In other tests, one has utilized the following reference proteins: thyroglobulin (330 kD), ferritin (220 kD), phosphorylase B (94 kD), bovine albumin (67 kD), catalase (60 kD), ovalbumin (43 kD), lactate dehydrogenase (36 kD), carbonic anhydrase (30 kD), an "inhibitor" (20.1 kD), ferritin (monomeric form) (18.5 kD), lactalbumin (14.4 kD). All these proteins are commercialized by PHARMACIA.

6. HUMAN SERUMS

The serums of two patients with visceral leishmaniosis, confirmed by the presence of parasites under direct examination, have permitted the completion according to the protocol cited previously, of the antigenic map. It was a matter of two infections, contracted in the Mediterranean area (Hérault and Algeria), having evolved respectively for 3 and 6 months.

RESULTS

1. CHOICE OF MONOCLONAL ANTIBODIES

After cloning by limit dilution of the positive hybrids, only 5 hybridomes secreting antibodies of the isotype IgG1 were retained. In immunofluorescence, they label the membrane of living promastigotes. These antibodies have then been produced in the mouse ascites.

2. INHIBITION TESTS

The inhibiting effect of monoclonal antibodies on the development of 4 species has been revealed by the absence of amastigotes in the sarcomatous cells infected intraperitoneally. Ten days after the injection, the transfer of the cells into NNN medium does not reveal the presence of promastigote forms. On the other hand, the couplings realized with the negative ascites or non-specific monoclonal antibodies are expressed by a continual infection, proved secondarily by multiplication of the promastigotes in vitro.

3. CHARACTERIZATION OF THE ANTIGENS

The antigens of the different species of Leishmanias able to be recognized by the mixture of inhibiting monoclonal antibodies, have been listed in the following table:

TABLE

| | Species | | | |
|---|---|---|---|---|
| | L. infantum | L. tropica | L. mexicana amazonensis | L. brasilien- guyanensis |
| molecular weight | 113 | 113 | 113 | 113 |
| | | | | 80 |
| | 70 | 70 | 70 | 70 |
| (in kilo-Daltons) | 68 | | | |
| | 48 | | 60 | 60 |
| | 44 | | 44 | 44 |
| | 40 | 40 | 40 | 40 |
| | | | 36 | 36 |

The underlined numbers indicate a strong reaction between antigen and antibody. It is important to emphasize that three antigens of molecular weights of 40 kD, 70 kD and 113 kD were continually recognized among the panoply of leishmanias of the Old and New world. Their corresponding antibodies permitting the prevention of infection by the promastigotes in the mouse, one may think that one or another of these antigens may play a role in the acquisition of a crossed immunoprotection. By way of comparison, the results of the immunoblotting realized with the serums of two leishmania patients have been equally colligated. They equally show an antigen of 70 kD, but not those of 40 kD and 113 kD. The recognition of more than 5 antigens in L. mexicana amazonensis and L. brasiliensis guyanensis suggests antigenic relationships between the different constituents of the strain.

It appears therefore that the antigen of 70 kD is:
(1) immunogenic in the mouse as well as in man,
(2) present in all the strains of leishmania studied.

In the same manner have been isolated the monoclonal antibodies which have proved to recognize a molecule of a molecular weight of around 140,000 in the lysates of several leishmanias. As shown again by the results of supplementary tests, one may equally isolate by the process according to the invention the hybridomes secreting monoclonal antibodies recognizing antigens having molecular weights less than 20,000 and apt in their turn to induce the production in vivo of antibodies protecting against the Leishmanias.

4. VACCINATION TESTS

Vaccination experiments in the Balb/c mice with extracts of promastigotes of L. infantum were conducted in the following fashion:

The promastigotes were lysed thus: the pellet of parasites was suspended in the buffer Tris 10 mM pH 7.5 containing detergents of the NP40 type (0.5%) and SDS (1%). The suspension obtained was then treated with ultrasound (sonicated) for 1 minute 30 seconds.

The homogenate has been resuspended in the sample buffer containing:
5% beta-mercapto-ethanol,
3% SDS,
0.065M Tris and
10% glycerol,
and deposited on a gel of polyacrylamide and sodium dodecylsulfate at 10% acrylamide (PAGE-SDS). After electrophoresis, a part of the gel was stained in order to reveal the protein bands and another part, not stained, was cut into 6 fractions named F1, F2. . . F6.

The ranges or regions of molecular weights corresponding to each fraction were the following (molecular weights appreciated according to the migration distances of the said proteins, compared to those of the proteins of molecular weights described above under the heading "ANTIGENIC CHARACTERIZATION":

| Fractions | Ranges of molecular weight |
|---|---|
| F1 | >94,000 daltons |
| F2 | between 94,000 and 67,000 daltons |
| F3 | between 67,000 and 43,000 daltons |
| F4 | between 43,000 and 30,000 daltons |
| F5 | between 30,000 and 20,000 daltons |
| F6 | less than 20,000 daltons. |

Each fraction was electro-eluted from the gel, then dialyzed, and lastly:
either lyophilized,
or conserved as is at −80 degrees C.

The possible protective activity of each of these fractions has been evaluated by the capacity of these fractions to induce in vivo the production of antibodies apt to inhibit in vivo the parasitic infection of the sarcomatous TG180 cells, in the tests realized according to the protocol described above under the heading "INHIBITION TESTS", except that the parasites have been pre-incubated with the serums obtained from animals (mice) immunized with the aforesaid fractions, before being placed in contact with the cells which have then been injected into the Balb/c mice.

One indicates hereafter the conditions in which the two lots of mice utilized have been immunized.

(a) Sub-cutaneously (5 mice/fraction)

Each mouse received 3 injections at one month of intervals, of 100 mg of stock fraction maintained at −80 degrees C. with 100 micrograms of muramyldipeptide (MDP).

The controls were done with 0.15M NaCl+100 micrograms MDP.

(b) Intravenously (8 mice/fraction)

Each mouse received 3 injections at one month of intervals of 100 micrograms of lyophilized stock fraction. The controls were done with 0.15M NaCl.

In every case, 3 months after the immunization, the serums of the immunized animals were drawn off and the serum of each animal was decomplemented, then utilized in the protection test previously described in the principal patent.

One has thus tested the protective effect of each mouse serum on the mixture of 4 strains of Leishmania (L. infantum, L. mexicana amazonensis, L. tropica and L. brasiliensis guyanensis).

In the table which follows and in which are indicated the protecting effects induced by the serums obtained in animals previously immunized by the fractions F1 to F6, one means by "complete protection with all the serums", the capacity for the serums in question to inhibit the parasitic infection of the sarcomatous cells of the TG180 line in all the animals of the groups concerned, when $2 \times 10^3$ cells of this line are injected into the peritoneum of immunized mice in combination with $10^5$ promastigotes non-pretreated by the serums.

The results are summarized in the following table:

| Fraction | Protective effect |
|---|---|
| F1 | no constant protection |
| F2 | complete protection with all the serums |
| F3 | no constant protection |
| F4 | no constant protection |
| F5 | complete protection with all the serums |
| F6 | complete protection with all the serums |
| control | no protection at all. |

These results are identical with serums of mouse immunized intravenously as well as sub-cutaneously.

In addition one has characterized the glucidic nature of the different fractions obtained from L. infantum lysate.

For this, a lysate of L. infantum has been resolved on PAGE-SDS gel at 10% acrylamide, under the same conditions as previously, then the electrophoretic profile was transferred onto nitrocellulose sheet.

The nitrocellulose sheet was cut into several strips of paper including all, after transfer, the aforesaid electrophoretic profile. Each strip of paper has been the object of a revelation with the aid of lectins conjugated to peroxydase and made by the technique of J. L. GUESDON and Col. (J. of Immunological Methods 39 (1980), 1–13). The following conjugates have been made:
(1) Conjugated lectin concavalin-peroxydase,
(2) Ulex europaeus-peroxydase
(3) Dolichos biflorus-peroxydase,
these different lectins being characterized by marked affinities respectively for:
(1) mannose, glucose,
(2) fucose and
(3) alpha-D-N-acetyl-galactosamine.

The paper is incubated 30 minutes with a dilution at 1/200th of the conjugated lectin, then after several washings in the presence of the wetting agent TWEEN 20 at 0.1%, one has revealed the presence of bound lectin by the presence of the associated peroxidase, by adding the substrates of this latter (hydrogen peroxide and diaminobenzidine). The presence of a brown precipitate on the paper permits the localization of the enzymatic activity.

The results were the following:

| lectin | band recognized | sugar concerned |
|---|---|---|
| ConA-PO | 85 kDaltons* | glucose, mannose |
| Ulex-PO | 85 kD | fucose |
|  | 30 kD* |  |
|  | 20 kD* |  |
| Dolichos-PO | 85 kD | alpha-D-N acetyl-galactosamine |
|  | 67 kD |  |
|  | 32 kD* |  |
|  | 20 kD* |  |

The molecular weights are estimated at 10%.

The results marked with an asterisk concern the bands which prove to be recognized by the antibodies of the animals immunized with the fractions containing the corresponding molecular weights.

The invention concerns consequently equally the immunogenic compositions characterized by the association of one at least of the above-indicated active fractions with a physiologically acceptable excipient permitting its administration to a living host, in view of conferring to it an immunity with regard not only to these polypeptide fractions, but equally to the pathogenic parasites.

One will note besides that the serums isolated from 20 patients have shown that the serums of only two patients recognized the 70 kD glycoprotein. This fact tends to show that, to be protected against leishmanioses, the human organisms should normally contain the antibodies formed against the 70 kD glycoprotein. Indeed, the absence of corresponding antibodies in the patients' serums may be explained by the slowness of the formation of protecting antibodies.

Conversely, the different fractions according to the invention may equally be utilized in a process for the detection of the presence of anti-leishmania antibodies, notably in blood samples coming from man or animals, for example to verify the existence or not of protection of the host against the leishmanioses.

The monoclonal antibodies according to the invention may equally be utilized as vehicles to transport a toxic molecule (for example gelonin) or an anti-parasite medicine and to concentrate it at the very sites of its action, more particularly the parasites themselves under their promastigote or amastigote form. Thus, the monoclonal antibodies according to the invention may be chemically coupled in a covalent fashion with the toxic substances or anti-leishmania medicinal substances. This covalent coupling naturally involves functional groups as well from the antibodies as from the medicines used which do not intervene in the antigen-antibody reaction, on the one hand, at the level of the action of the substances, on the other hand. Appropriate medications have been considered in the international application WO83/01785. In one advantageous form of conjugates susceptible of being used, the medication is encapsulated in liposomes, these being themselves covalently bound to the antibodies, for example by the intermediary of N-succinimidyl-3-(2-pyridyl-dithio)-propionate (SPDP): see notably J. Biol. Chem. 255, 2015-2018 (1980); Nature, vol. 293, No. 5829, p. 228, 1981 and J. of Supramolecular Structure and Cellular Biochemistry 16, p. 243-258 (1981).

The monoclonal antibodies according to the invention may equally be utilized to purify the polypeptide compositions susceptible of containing immunogenic proteins, such that the antigens of molecular weights of 40,000, 70,000, 113,000 or 140,000 daltons, according to the nature of the antibodies utilized. This process is advantageously applied to extracts obtained from the parasites (for example lysates of parasites). It may also be applied to the extraction of these polypeptides from the supernatants of the culture mediums of these parasites, when these supernatants are susceptible of containing such polypeptides as metabolism products of the said parasites. For the operation of this process, the monoclonal antibodies are advantageously immobilized on a solid support, preferably adapted to the operations of affinity chromatography. For example, these monoclonal antibodies are bound onto a three-dimensional network of cross-linked agarose commercialized under the trademark SEPHAROSE by the Swedish company PHARMACIA A.G., for example by the cyanogen bromide method.

The invention concerns more particularly a process for the separation of these antigens characterized by operations consisting of passing the medium susceptible of containing them (notably parasite extract or growth medium of these parasites) into contact with an affinity column bearing the aforesaid monoclonal antibodies, to selectively bind the said polypeptides, then to recuperate them by dissociation from the antigen-antibody complex by means of an appropriate buffer, notably of a solution of adequate ionic strength, notably of a salt, preferably ammonium acetate (which does not leave a residue when one then realizes the lyophilization of the preparation). One may equally have recourse to a solution acidified to pH 3-4 or to a glycine buffer at the same pH.

The invention equally concerns the polypeptides common to several Leishmanias, and more particularly those which are recognized by the monoclonal antibodies secreted by the hybridome strains which have been filed with the 'Collection Nationale des Cultures de Microorganismes' (C.N.C.M.) of the INSTITUT PASTEUR of Paris, under the numbers I-344 and I-345 the 1st of October 1984.

The invention concerns more particularly yet among these polypeptides those among them, notably that which presents a molecular weight of the order of 70,000—or those having ranges of molecular weights of 67,000-94,000 daltons, or again those having molecular weights less than 20,000 daltons, which are equally recognized by the serums coming from human patients having leishmanioses.

These polypeptides or antigens are themselves capable of being utilized as reagents, or even as diagnostic agents in vitro, for the detection of anti-Leishmania antibodies. It goes without saying that the invention concerns equally the polypeptide fractions which may have lower molecular weights, once they carry antigenic sites susceptible of being recognized by the same monoclonal antibodies. It will appear clearly to the specialist that starting from the moment that one has the monoclonal antibodies according to the invention, one may consider the isolation, starting from the antigens indicated above, of the smaller peptide sequences containing the same antigenic sites, for example in having recourse to techniques in themselves known of sequencing the initial polypeptide by the enzymes susceptible of cleaving larger polypeptides in specific sites. By way of example of such proteins, one may mention the enzyme from *Staphylococcus aureus* VS, alpha-chymotrypsin, mouse submaxillary glad protease commercialized by the BOEHRINGER company, the collagenase of *Vibrio alginolyticus chemovar iophaqus*, which specifically recognizes the said peptides Gly-Pro and Gly-Ala, etc.

The polypeptides of the type in question may equally be used to separate the antibodies presenting the characteristics indicated above starting from a mixture of polyclonal antibodies. In this case, polypeptides of the kind in question will in their turn be immobilized on an affinity chromatography support, for example of the type indicated above. The separation process will consequently include the step consisting of passing the medium containing the polyclonal antibodies into contact with the immobilized polypeptides, and the step of recuperation of the retained antibodies by means of a solution or of a buffer analogous to that which has been discussed above.

Lastly the invention concerns the immunogenic compositions characterized by the association of one of the immunogenic antigens indicated above with a physiologically acceptable excipient permitting its administration to a living host, in view of conferring to it an immunity with regard to the said polypeptides. These polypeptides constitute the active principles of which the immunogenicity may be invoked each time that in vivo protection against parasites in sought.

The invention concerns equally a process utilizing the antigens recognized by the aforesaid monoclonal antibodies for the detection of the presence of anti-Leishmania antibodies, notably in blood samples coming from man or animals, in view of detecting the infection.

In one variant of this process, the detection of the presence of anti-Leishmania antibodies brings into play reactions of hypersensitivity (intradermic reactions) necessary to the diagnosis of the infection in man or animals.

As it goes without saying and as it results, by the way, already from that which precedes, the invention is in no way limited to those of their modes of application and execution which have been more especially foreseen; it embraces on the contrary all the variants; as an alternative, the invention concerns a process utilizing the infection of the sarcomatous TG180 cells by the parasites (amastigote form) to determine the efficacy of new antibody forms (mono- or polyclonal) to arrest the parasitic infection. The same test may be utilized to determine the efficacy of the new anti-Leishmaniosis medicinal molecules.

The sarcomatous TG180 cell strain has been deposited with the CNCM (Collection Nationale des Cultures de Micro-organismes of the INSTITUT PASTEUR) under the number I-343, the 26th of September 1984.

The parasite strain *L. infantum* (LEM 497) which has been utilized in the initial immunization of the mice in view of the productionm of the monoclonal antibodies more particularly described in the examples, has been deposited with the CNCM the 26th of September 1984 under the number I-342.

It is intended that when one has made use of the word "leishmanias", it is naturally the parasites of the genus Leishmania which are referred to.

We claim:

1. Antigens of leishmania parasites, having molecular weights on the order of 20,000, 40,000, 70,000, 113,000 or 140,000 daltons and being recognized by the monoclonal antibodies secreted by the hybridomes deposited with the C.N.C.M. under numbers I-344 and I-345; said antigens inducing the in vivo production in mice of protective antibodies against a plurality of leishmaniae; said antibodies inhibiting the infection of mouse sarcomatous cells of a TG180 line, deposited with the C.N.C.M. under number I-343, when $2\times 10^3$ cells of said TG180 line are injected into the peritoneum of mice, mixed with $10^5$ promastigotes of a plurality of strains of leishmania; said promastigotes having previously been incubated with said antibodies.

2. The antigens according to claim 1 characterized in that they are recognized by the human serums containing antibodies with regard to the leishmanias.

3. The antigens according to claim 1 characterized in that they contain a protective glycoprotein having a molecular weight of the order of 70 kD and including glucose and mannose groups.

4. The antigens according to claim 1 characterized in that they contain glycoproteins isolatable from lysates of the leishmanias presenting molecular weights of the order of 20 kD and containing fucose and alpha-D-N-acetyl-galactosamine groups.

5. The antigens according to claim 1 characterized in that they contain glycoproteins isolatable from lysates of the leishmanias presenting molecular weights of the order of 30–32 kD and containing fucose and alpha-D-N-acetyl-galactosamine groups.

6. The antigens of claim 1 wherein said promastigotes are incubated with said antibodies by contacting said promastigotes at 37° C. for 30 minutes with a sera from a Balb/c mouse immunized with said antigens; and thereafter, said promastigotes are injected with said cells of said TG180 line into a Balb/c mouse.

7. The antigens of claim 1 wherein said promastigotes are of the *L. infantum* strain deposited with the CNCM under number I-342.

8. The antigens of claim 1 having molecular weights on the order of 40,000, 70,000 or 113,000.

9. A immunogenic composition against leishmania parasites comprising one or more antigens of claim 1 and a sterile, pharmaceutically acceptable vehicle.

10. A immunogenic composition against leishmania parasites comprising one or more antigens of claim 8 and a sterile, pharmaceutically acceptable vehicle.

* * * * *